United States Patent [19]

Johnson et al.

[11] Patent Number: 5,141,934

[45] Date of Patent: Aug. 25, 1992

[54] TETRACYCLIC AMINES HAVING PHARMACEUTICAL ACTIVITY

[75] Inventors: Graham Johnson, Ann Arbor; Thomas C. Malone, Canton, both of Mich.

[73] Assignee: Warner-Lambert Company, Morris Plains, N.J.

[21] Appl. No.: 605,815

[22] Filed: Oct. 30, 1990

[51] Int. Cl.$^5$ .................. C07D 487/08; A61K 31/55
[52] U.S. Cl. .................................... 514/214; 540/581
[58] Field of Search ....................... 540/581; 514/214

[56] References Cited

U.S. PATENT DOCUMENTS

| | | | |
|---|---|---|---|
| 3,509,158 | 4/1970 | Dobson et al. | 540/581 |
| 3,597,433 | 8/1971 | Dobson et al. | 540/581 |
| 4,869,791 | 9/1989 | Karady | 204/72 |
| 4,870,079 | 9/1989 | Britcher et al. | 514/289 |
| 4,870,080 | 9/1989 | Lamanec et al. | 514/289 |
| 4,940,789 | 7/1990 | Childers, Jr. et al. | 540/581 |

FOREIGN PATENT DOCUMENTS 0230370 7/1987 European Pat. Off. .
0303421 2/1989 European Pat. Off. .

OTHER PUBLICATIONS

Thompson et al, J. Med. Chem. 1990, 33, 789.
Monn, et al, J. Med. Chem. 1990, 33, 1069.
Lyle, et al, J. Med. Chem. 1990, 33, 1047.
Chem Abs., vol. 51, 10523f (1957).
Harasawa, et al, 1957, 77, 794, Yakugaka Zasshi.
Ochiai, Chem. Pharm. Bulletin, 1955, 369.
Chem. Abs., vol. 51, 10515a, 1957.

*Primary Examiner*—C. Warren Ivy
*Assistant Examiner*—Catherine S. Kilby Scalzo
*Attorney, Agent, or Firm*—Elizabeth M. Anderson

[57] ABSTRACT

The present invention relates to novel tetracyclic amines and derivatives thereof useful as pharmaceutical agents, to methods for their production, to pharmaceutical compositions which include these compounds and a pharmaceutically acceptable carrier, and to pharmaceutical methods of treatment. The compounds of the present invention are useful in the treatment of neurodegenerative disorders including cerebrovascular disorders.

8 Claims, No Drawings

TETRACYCLIC AMINES HAVING PHARMACEUTICAL ACTIVITY

BACKGROUND OF THE INVENTION

The present invention relates to novel tetracyclic amines and derivatives thereof useful as pharmaceutical agents, to methods for their production, to pharmaceutical compositions which include these compounds and a pharmaceutically acceptable carrier, and to pharmaceutical methods of treatment. The compounds of the present invention are useful in the treatment of neurodegenerative disorders including cerebrovascular disorders.

Excessive excitation by neurotransmitters can cause the degeneration and death of neurons. It is believed that this degeneration is in part mediated by the excitotoxic actions of glutamate and aspartate at the N-methyl-D-aspartate (NMDA) receptor. This excitotoxic action is responsible for the loss of neurons in cerebrovascular disorders such as: cerebral ischemia or cerebral infraction resulting from a range of conditions such as thromboembolic or hemorrhagic stroke, cerebral vasospasm, hypoglycemia, cardiac arrest, status epilepticus, perinatal asphyxia, anoxia such as from drowning, pulmonary surgery and cerebral trauma.

There are no specific therapies for these neurodegenerative diseases, however, compounds which act specifically as antagonists of the NMDA receptor complex, either competitively or noncompetitively, offer a novel therapeutic approach to these disorders: R. Schwarcz and B. Meldrum, *The Lancet* 140 (1985); B. Meldrum in "Neurotoxins and Their Pharmacological Implications" edited by P. Jenner, Raven Press, New York (1987); D. W. Choi, Neuron 1:623 (1988). Confirmation of the protective effects of noncompetitive NMDA antagonists in various pharmacological models of neurodegenerative disorders have appeared in the literature: J. W. McDonald, F. S. Silverstein, and M. V. Johnston, *Eur. J. Pharmocol.* 140:359 (1987); R. Gill, A. C. Foster, and G. N. Woodruff, J. Neurosci. 7:3343 (1987); S. M. Rothman, J. H. Thurston, R. E. Hauhart, G. D. Clark, and J. S. Soloman, Neurosci. 21:673 (1987); M. P. Goldbert, P-C. Pham, and D. W. Choi, *Neurosci. Lett.* 80:11 (1987); L. F. Copeland, P. A. Boxer, and F. W. Marcoux, Soc. Neurosci. Abstr. 14 (part1):420 (1988); J. A. Kemp, A. C. Foster, R. Gill, and G. N. Woodruff, *TIPS* 8:414 (1987); R. Gill, A. C. Foster, and G. N. Woodruff J. Neurosci. 25:847 (1988); C. K. Park, D. G. Nehls, D. I. Graham, G. M. Teasdale, and J. M. McCulloch, *Ann. Neurol.* 24:543 (1988); G. K. Steinburg, C. P. George, R. DeLaPlaz, D. K. Shibata, and T. Gross, *Stroke* 19:1112 (1988); J. F. Church, S. Zeman, and D. Lodge, *Anesthesiology* 69:702 (1988).

European Patent Application 230,370 discloses certain 5 substituted-10,11-dihydro-5H-dibenzocyclohepten-5,10 imines and analogues thereof useful for preventing or treating neurodegenerative disorders. The further preparation of these compounds is described by W. J. Thompson et al in *J. Med. Chem.* 33, 789 (1990) and K. C. Rice et al in *J. Med. Chem.* 33, 1069 (1990) The preparation of certain polyhydro derivatives of 10,11-dihydro-5H-benzo(a,d)cyclohepten-5,10-imines and their evaluation as N-methyl-D-aspartate antagonists are disclosed in European Patent Application 303,421, U.S. Pat. Nos. 4,869,791, 4,870,079, and 4,870,080 and by T. A. Lyle et al in *J. Med. Chem.* 33, 1047 (1990). The syntheses and reactions of N-methyl-15-aza-des-N-morphinan are described by K. Harasawa in *Yakugaku Zasshi* 77, 168 (1957), *Yakugaku Zasshi* 77 794 (1957) and *Chem. Pharm. Bull.* 3 369 (1955). The optical resolution of N-methyl-15-aza-des-N-morphinan and description of its analgesic activity is described by K. Harasawa in *Yakugaku Zasshi* 77, 172 (1957). However, none of the aforementioned publications teaches nor suggests the compounds of the present invention.

SUMMARY OF THE INVENTION

The present invention provides compounds of the formula

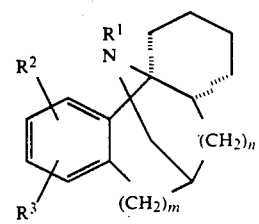

or a pharmaceutically acceptable acid addition salt thereof wherein $R^1$, $R^2$, $R^3$, m, and n are as described hereinbelow.

The present invention also includes a pharmaceutical composition comprising a therapeutically effective amount of a compound of formula I together with a pharmaceutically acceptable carrier.

The present invention also includes a method for treating cerebrovascular disorders which comprises administering to a patient in need thereof the above pharmaceutical composition in unit dosage form.

The present invention also includes a method for treating disorders responsive to the blockade of glutamic and aspartic acid receptors comprising administering to a patient in need thereof a therapeutically effective amount of the above composition.

The invention also includes a method for treating cerebral ischemia, cerebral infarction, cerebral vasospasm, hypoglycemia, cardiac arrest, status epilepticus, cerebral trauma, schizophrenia, epilepsy, neurodegenerative disorders, Alzheimer's disease, or Huntington's disease comprising administering to a patient in need thereof a therapeutically effective amount of the above composition.

The invention also includes a method for treating stroke in patients in need thereof which comprises administering to a patient in need thereof a therapeutically effective amount of the above composition.

The invention also includes using as an anesthetic the above composition in surgical operations where a risk of cerebrovascular damage exists.

The invention further includes processes for the preparation of compounds of formula I.

The invention still further includes novel intermediates useful in the processes.

DETAILED DESCRIPTION

The present invention provides compounds of the formula

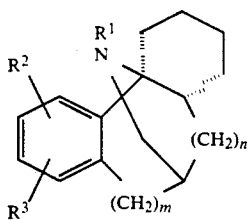

or a pharmaceutically acceptable acid addition salt thereof wherein:

$R^1$ is hydrogen, loweralkyl, loweralkenyl, loweralkynyl, arylloweralkyl, cycloalkylloweralkyl, or a pharmaceutically acceptable labile group, $R^2$ and $R^3$ are each independently hydrogen, loweralkyl, hydroxy, loweralkoxy, trifluoromethyl, halogen, amino, monoloweralkyl, or diloweralkylamino, m and n are each independently 0, 1, or 2.

Preferred compounds of the instant invention are those of formula I wherein:

$R^1$ is hydrogen, loweralkyl, loweralkenyl, or cyclopropylmethyl $R^2$ and $R^3$ are each independently hydrogen, loweralkyl hydroxy, or loweralkoxy, m and n are each independently 0 or 1.

More preferred compounds of the instant invention are those of formula I wherein $R^1$ is hydrogen, loweralkyl, loweralkenyl, or cyclopropylmethyl, $R^2$ and $R^3$ are each independently hydrogen, loweralkyl hydroxy, or loweralkoxy, m is 0 when n is 1 and m is 1 when n is 0.

Still more preferred compounds of the instant invention include but are not limited to:

(+), (−), or (+/−)-(4aα,10α,10aα)-1,3,4,9,10,10a-hexahydro-2H-4a,10-(iminomethano)phenanthrene, (+), (−), or (+/−)-(4aα,10α,10aα)-1,3,4,9,10,10a-hexahydro-6-methoxy-2H-4a,10-(iminomethano)-phenanthrene, (+), (−), or (+/−)-(4aα,10α,10aα)-1,3,4,9,10,10a-hexahydro-12-methyl 2H-4a,10-(iminomethano)-phenanthrene, (+), (−), or (+/−)-(4aα,10α,10aα)-1,3,4,9,10,10a-hexahydro-6-methoxy-12 methyl-2H 4a,10-(iminomethano)-phenanthrene, (+), (−), or (+/−)-(4aα,10α,10aα) 12-ethyl-1,3,4,9,10,10a-hexahydro-2H-4a,10-(iminomethano)-phenanthrene, (+), (−), or (+/−)-(4aα,10α,10aα)-1,3,4,9,10,10a-hexahydro-12-propyl-2H-4a,10-(iminomethano)-phenanthrene, (+), (−)-, or (+/−)-(4aα,10α,10aα) 12-(cyclopropylmethyl)-1,3,4,9,10,10a-hexahydro 2H-4a,10-(iminomethano)phenanthrene, (+), (−), or (+/−)-(4aα,10α,10aα)-1,3,4,9,10,10a-hexahydro-12-(2 propenyl)-2H-4a,10-(iminomethano)-phenanthrene, (+), (−), or (+/−)-(4aα,10α,10aα) 1,3,4,9,10,10a-hexahydro-2H-4a,10-(iminomethano)phenanthren-6-ol, (+), (−), or (+/−)-(4aα,10α,10aα) 1,3,4,9,10,10a-hexahydro-12-methyl 2H-4a,10-(iminomethano)-phenanthren-6-ol, (+), (−), or (+/−)-(4aα,9α,10aα) 1,3,4,9,10,10a-hexahydro-2H-4a,9-(iminomethano)phenanthrene, (+), (−), or (+/−)-(4aα,9α,10aα)-1,3,4,9,10,10a-hexahydro-6-methoxy 2H-4a,9-(iminomethano)-phenanthrene, (+), (−), or (+/−)-(4aα,9α,10aα)-1,3,4,9,10,10a-hexahydro-12-methyl-2H-4a,9-(iminomethano)-phenanthrene, (+), (−), or (+/−)-(4aα,9α,10aα)-1,3,4,9,10,10a-hexahydro-12-methyl-6-methoxy-2H-4a,9-(iminomethano)-phenanthrene, (+), (−), or (+/−)-(4aα,9α,10aα)-1,3,4,9,10,10a-hexahydro-2H-4a,9-(iminomethano)phenanthren-6 ol, and (+), (−), or (+/−)-(4aα,9α,10aα)-1,3,4,9,10,10a-hexahydro-12-methyl-2H-4a,9-(iminomethano)phenanthren-6-ol.

Loweralkyl means a straight chained or branched chain of from one to four carbon atoms including but not limited to methyl, ethyl, propyl, butyl.

Loweralkenyl means a group from two to four carbon atoms, for example, but not limited to ethylene, 1,2- or 2,3-propylene, 1,2- 2,3-, or 3,4-butylene.

Loweralkynyl means a group from two to four carbon atoms, for example, but not limited to ethynyl, 2,3-propynyl, 2,3-, or 3,4-butynyl; propynyl is the preferred group.

Cycloalkylloweralkyl means cycloalkyl of from three to six carbon atoms and lower alkyl as above, meaning for example, cyclopropylmethyl, cyclobutylmethyl, cyclopentylmethyl; cyclopropylmethyl is the preferred group.

Loweralkoxy means a group of from one to four carbon atoms, for example, but not limited to methoxy, ethoxy, propoxy; methoxy is the preferred group.

Halogen is fluorine, chlorine, bromine, or iodine; fluorine, chlorine and bromine are the preferred groups.

Arylloweralkyl means aryl such as phenyl, thienyl, pyridyl or the like, and alkyl as defined above, for example, benzyl, 2-phenylethyl, 3-phenylpropyl; preferred groups are benzyl.

Monoloweralkylamino means a group containing from one to four carbon atoms, for example, but not limited to methylamino, ethylamino, n- or i- (propylamino or butylamino).

Diloweralkylamino means a group containing from one to four carbon atoms in each lower alkyl group, for example, but not limited to dimethylamino, diethylamino, di-(n-propyl)-amino, di-(n-butyl)-amino, or may represent a fused ring, for example piperidine Physiologically labile group includes but is not limited to such derivatives described by; I. H. Pitman in *Med. Chem. Rev.* 2:189 (1981); J. Alexander, R. Cargill, S. R. Michelson and H. Schwam in *J. Med. Chem.* 31:318 (1988); V. H. Naringrekar and V. J. Stella in European Patent Application 214,009 and include certain amides, such as amides of amino acids, for example, glycine or serine, enaminone derivatives and (acyloxy)alkylcarbamates.

Well known protecting groups and their introduction and removal and described, for example, in J. F. W. McOmie, *Protective Groups in Organic Chemistry*, Plenum Press, London, New York (1973), and T. W. Greene, *Protective Groups in Organic Synthesis*, Wiley, New York (1981).

The compounds of the present invention contain asymmetric carbon atoms. The instant invention includes the individual diastereomers and enantiomers, which may be prepared or isolated by methods known to those skilled in the art.

Any resulting racemate can be resolved into the optical antipodes by known methods, for example by separation of the diasteromeric salts thereof, with an optically active acid, and liberating the optically active amine compound by treatment with a base. Racemic compounds of the present invention can thus be resolved into their optical antipodes e.g., by fractional crystallization of d- or l-(tartarates, mandelates, or camphorsulfonate) salts. The compounds of the instant invention may also be resolved by the formation of diastereomeric amides by reaction the compounds of the instant invention with an optically active activated carboxylic acid such as that derived from (+) or (−) phenylalanine, (+) or (−) phenylglycine, (+) or (−)-camphanic acid or by the formation of diastereomeric carbamates by reaction of the compounds of the instant invention with an optically active chloroformate or the like.

Additional methods for resolving optical isomers, known to those skilled in the art may be used, for example those discussed by J. Jaques, A. Collet, and S. Wilen in *Enantiomers, Racemates, and Resolutions*, John Wiley and Sons, New York (1981).

Salts of the compounds of the invention are preferably pharmaceutically acceptable salts. The compounds of the invention are basic amines from which acid addition salts of pharmaceutically acceptable inorganic or organic acids such as strong mineral acids, for example, hydrohalic, e.g., hydrochloric or hydrobromic acid; sulfuric, phosphoric or nitric acid; aliphatic or aromatic carboxylic or sulfonic acids, e.g., acetic, propionic, succinic, glycolic, lactic, malic, tartaric, gluconic, citric, ascorbic, maleic, fumaric, pyruvic, pamoic, nicotinic, methanesulfonic, ethanesulfonic, hydroxyethanesulfonic, benzenesulfonic, p-toluenesulfonic, or napthlenesulfonic acid can be prepared.

The compounds of the instant invention exhibit valuable pharmacological properties by selectively blocking the N-methyl-D-aspartate sensitive excitatory amino acid receptors in mammals. The compounds are thus useful for treating diseases responsive to excitatory amino acid blockade in mammals.

Such disorders include but are not limited to cerebral ischemia or cerebral infraction resulting from a range of conditions such as thromboembolic or hemorrhagic stroke, cerebral vasospasm, hypoglycemia, cardiac arrest, status epilepticus, perinatal asphyxia, anoxia such as from drowning, pulmonary surgery, and cerebral trauma. Other treatments are for schizophrenia, epilepsy, spasticity, neurodegenerative disorders such as Alzheimer's disease or Huntingtons disease, Olivo-pontocerebellar atrophy, spinal cord injury, and poisoning by exogenous NMDA poisons (e.g., some forms of lathyrism). Further uses are as analgesics and anesthetics, particularly for use in surgical procedures where a finite risk of cerebrovascular damage exists.

The effects are demonstrable in in vitro tests or in vivo animal tests using mammals or tissues or enzyme preparations thereof, e.g., mice, rats, or monkeys. The compounds are administered to patients enterally or parenterally, for example, orally, transdermally, subcutaneously, intravenously, or intraperitoneally. Forms include but are not limited to gelatin capsules, or aqueous suspensions or solutions. The applied in vivo dosage may range between about 0.01 to 100 mg/kg, preferably between about 0.05 and 50 mg/kg, most preferably between about 0.1 and 10 mg/kg.

The ability of the compounds of the instant invention to interact with phencyclidine (PCP) receptors which represents a noncompetitive NMDA antagonist binding site, is shown in Table 1. Tritiated 1[1-(2 thienyl)cyclohexyl]piperidine (TCP) binding, designated RBS1, was carried out essentially as described in *J. Pharmacol. Exp. Ther.*, 238, 739 (1986).

TABLE 1

| Example | n | m | $R^1$ | $R^2$ | $R^3$ | RBS1 IC$_{50}$ (nM) |
|---|---|---|---|---|---|---|
| 14 | 0 | 1 | H | H | H | 86 |
| 16 | 0 | 1 | CH$_3$ | H | H | 137 |
| 19 | 0 | 1 | Propyl | H | H | 54 |
| 20 | 0 | 1 | ⟨cyclopropylmethyl⟩ | H | H | 51 |
| PCP | | | (Reference Standard) | | | 40 |
| TCP | | | (Reference Standard) | | | 9 |
| Ketamine | | | (Reference Standard) | | | 860 |
| MK-801 | | | (Reference Standard) | | | 3 |

Methods of synthesis of the compounds of the instant invention are illustrated in Schemes A and B. The preparation of compounds of the formula I wherein m is 1, n is 0 and $R^1$, $R^2$, and $R^3$ are as previously defined are illustrated in Scheme A.

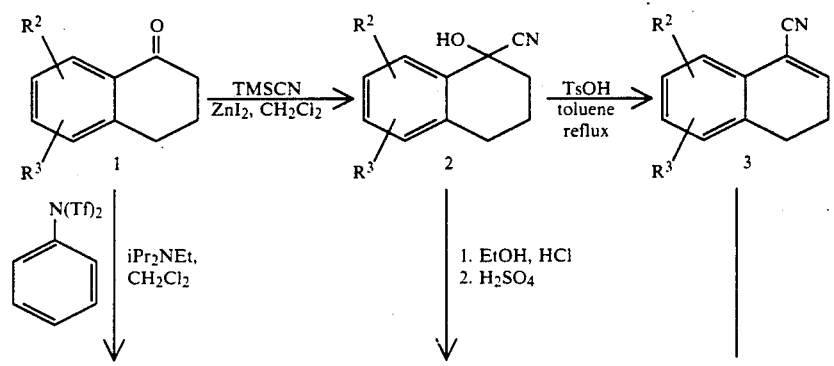

SCHEME A

-continued
SCHEME A
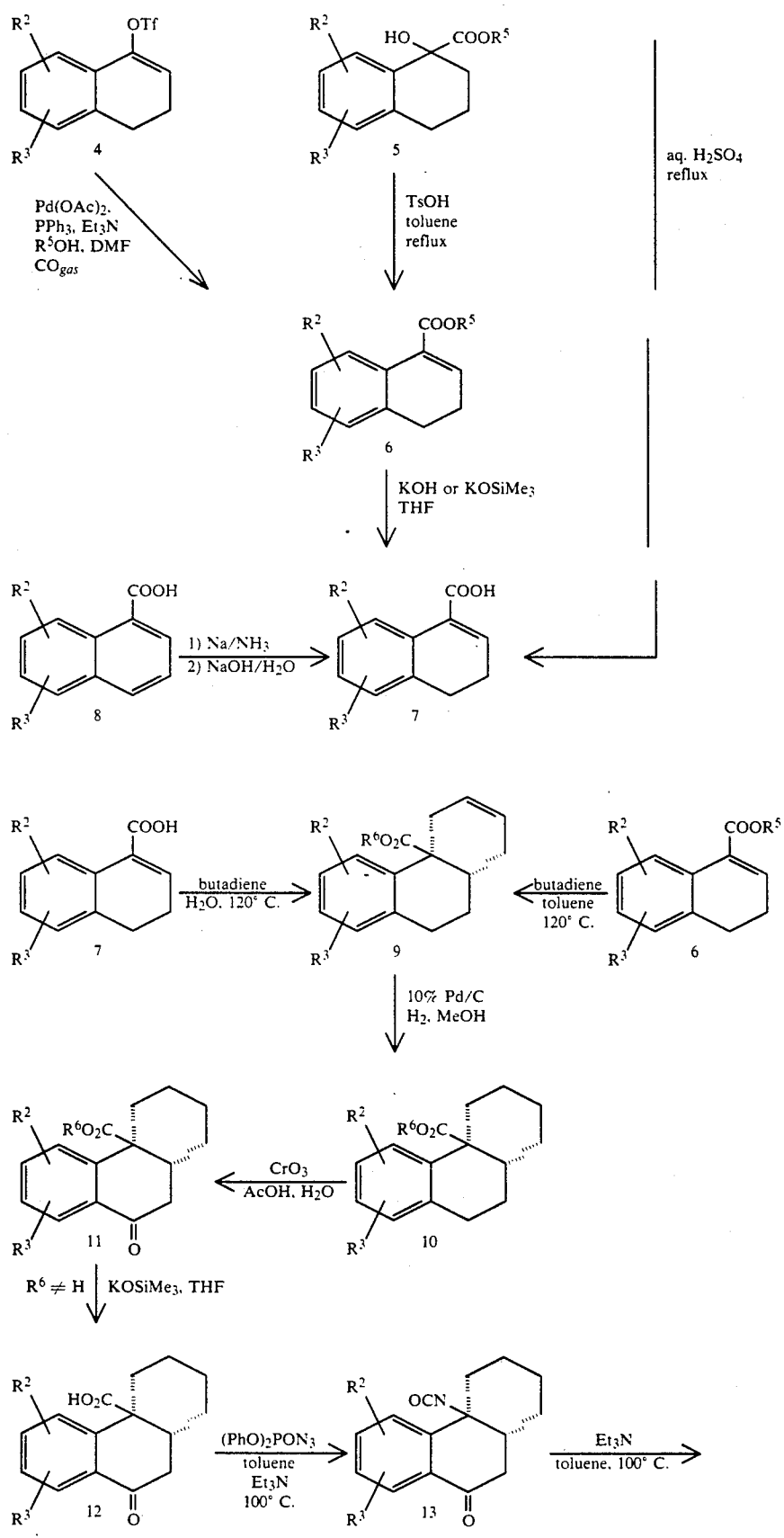

SCHEME A

-continued

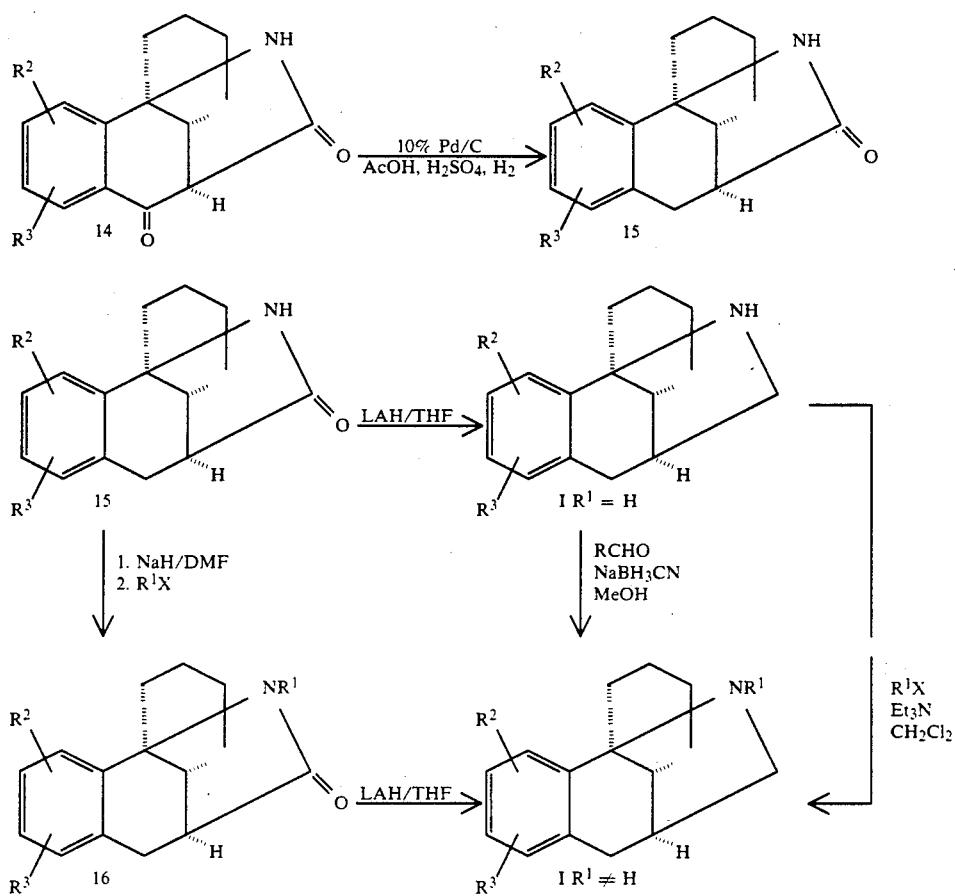

The saturated intermediate tricyclic acids (10, $R^6=H$) are available by an annulation process illustrated by G. Shina et al, in *J. Chem. Soc. Perkin Trans.* 1, 2519 (1983). The unsaturated tricyclic esters or acids (9, $R^6=H$, loweralkyl) may also be prepared by a Diels-Alder reaction of unsaturated esters (6, $R^5=$loweralkyl) or unsaturated acids (7) which may be prepared by a variety of methods from ketones (1) or by dissolving metal reduction of napthlene carboxylic acids (8) as described by Birch et al in *J. Chem. Soc.* 430 (1944) The Diels-Alder reactions may be carried out neat or in a solvent, preferably water or toluene, in the presence of a free radical inhibitor such as butylated hydroxytoluene at temperatures between 100° and 250° C., preferably 120°-180° C. Hydrogenation of the olefin in (9, $R^6=H$, loweralkyl) is accomplished by methods known to those who are skilled in the art, for example, by catalytic hydrogenation over a palladium on carbon catalyst to produce (10). The intermediate keto-ester (11) or keto-acid (12) may be prepared by chromium trioxide oxidation of (10) utilizing the method of R. Rangarajan and E. Eisenbraun in *J. Org. Chem.* 2435 (1985). Keto-ester (11, $R^6=$loweralkyl) may be converted to keto-acid (12) by hydrolysis.

The conversion of keto acid (12) to isocyanate (13) is accomplished by treatment of the acid with diphenylphosphoryl azide and a trialkylamine base, for example, triethylamine, in a solvent such as benzene or toluene or by conversion of the keto acid (12) to its corresponding acid chloride, followed by treatment with sodium or potassium azide in a solvent such as benzene in the presence of a phase transfer catalyst, for example, 18-crown 6. Continued heating of the aforementioned reactions will afford the tetracyclic ketoamide (14). Alternatively, the isocyanate (13) may be isolated and then heated in the presence of a base such as triethylamine in a solvent such as benzene or toluene at temperatures between 80 and 150° C. to afford tetracyclic ketoamide (14). Hydrogenation of the ketoamide (14) using a palladium on carbon catalyst in a solvent such as acetic acid containing sulfuric acid provided tetracyclic amide (15).

The compounds of the instant invention may be derived from the tetracyclic amides (15) by reduction of the amide functionality using lithium aluminum hydride, diborane, or the like, in a solvent such as tetrahydrofuran, ether, or the like. The tetracyclic amines (I, $R^1=H$) may be N-alkylated by reductive amination, for example, by treatment of tetracyclic amines (I, $R^1=H$) with an aldehyde or a ketone, in the presence of sodium cyanoborohydride in a solvent such as methanol, ethanol or the like to give N-alkylated amines (I, $R^1 \neq H$). Tetracyclic amines (15) may also be N-alkylated by treatment with an alkylating agent, for example, allyl or benzyl bromide. Alternatively alkylation of tetracyclic amides (15) followed by reduction of the N-alkylated tetracyclic amides (16) using lithium aluminum hydride or diborane, in a solvent such as ether or tetrahydrofuran may provide N-alkylated tetracyclic amines (I, $R^1 \neq H$).

The preparation of compounds of the formula I wherein m is 0 and n is 1 are illustrated in Scheme B.
SCHEME B
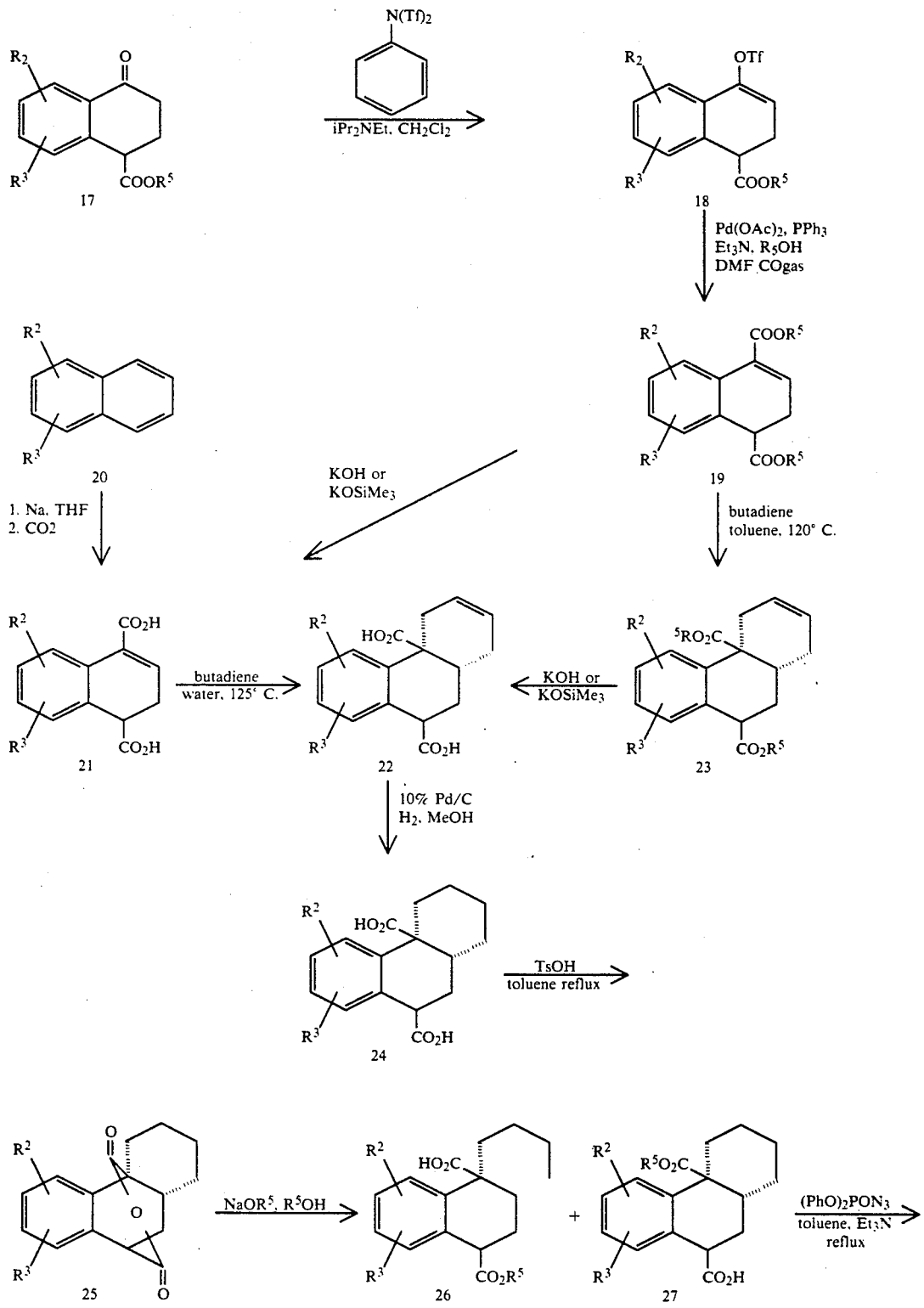

-continued
SCHEME B

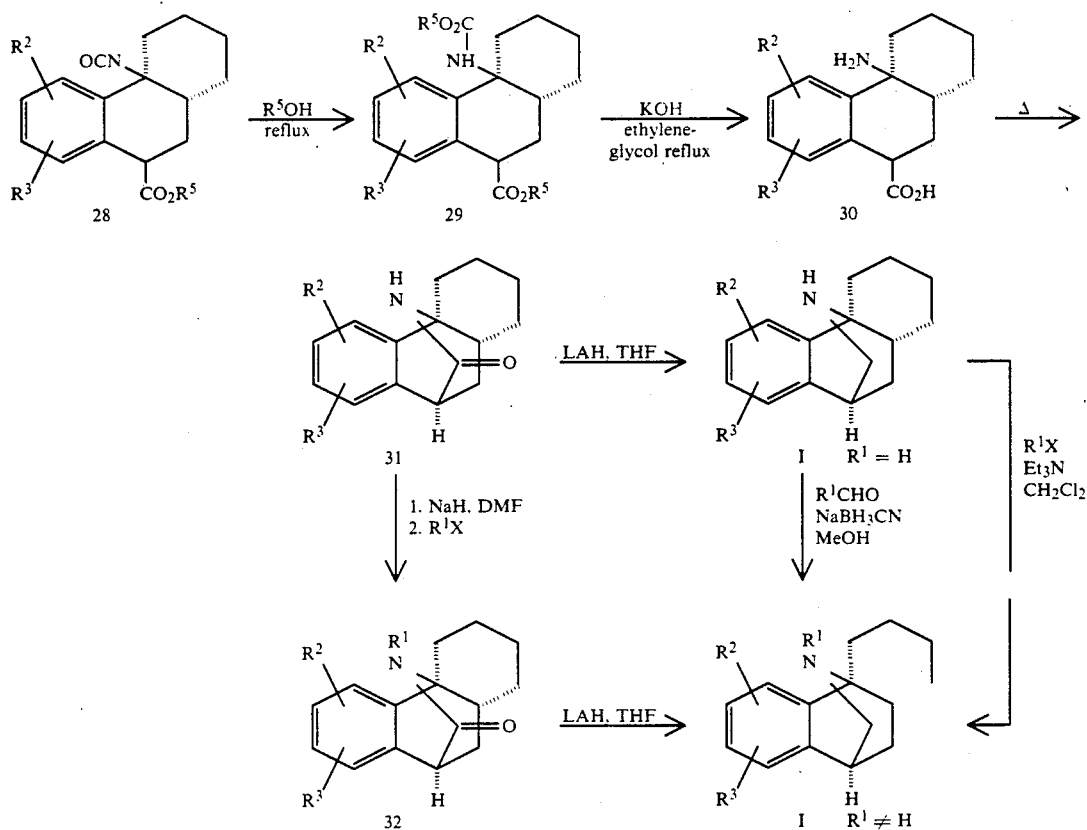

The intermediate unsaturated diesters (19) may be prepared by a palladium mediated carbonylation reaction of unsaturated triflate (18) using methodology described by G. Ortar et al in *Tetrahedron Lett.* 26, 1109 (1985). Hydrolysis of diester (19) may provide diacid (21). Alternatively, Birch reduction of substituted naphthlenes (20) followed by carbonylation with carbon dioxide as described by Lyssy in *J. Org. Chem.* 5 (1962) may provide diacids (21).

The unsaturated tricyclic diesters (23) or diacids (22) may be prepared by Diels-Alder reaction of unsaturated diesters (19) or diacids (21) with butadiene in a solvent, preferably water or toluene in the presence of a free radical inhibitor such as butyrated hydroxytoluene. Hydrolysis of unsaturated tricyclic diester (23) may provide (22). Hydrogenation of the unsaturated tricyclic diacids (22) with palladium on carbon catalyst may provide the tricyclic diacids (24). The anhydride (25) may be formed by treatment of tricyclic diacids (24) with a sulfonic acid catalyst such as toluenesulfonic acid, camphorsulfonic acid, or the like in a solvent such as benzene, toluene or the like with azeotrophic removal of water. Treatment of the tetracyclic anhydride (25) with sodium methoxide in methanol, or sodium ethoxide in ethanol, or the like may provide a mixture of esters (26) and (27).

Treatment of the acid (26) with diphenylphosphoryl azide and a trialkylamine base, for example, triethylamine, in a solvent such as benzene or toluene or by conversion of the acid (26) to its corresponding acid chloride, followed by treatment with sodium azide in a solvent such as benzene in the presence of a phase transfer catalyst, for example, 18-crown-6 may provide isocyanate (28). Treatment of isocyanate (28) with an alcohol provides tricyclic carbamate (29). Hydrolysis of carbamate (29) provides amino-acid (30). The tetracyclic amide (31) may be prepared by heating amino-acid (30) either neat or in a solvent such as xylenes.

The compounds of the instant invention may be derived from the tetracyclic amides (31) by reduction of the amide functionality using lithium aluminum hydride, diborane, or the like, in a solvent such as tetrahydrofuran, ether, or the like. The tetracyclic amines (I, $R^1=H$) may be N-alkylated by reductive amination, for example, by treatment of tetracyclic amines (I, $R^1=H$) with an aldehyde or a ketone, in the presence of sodium cyanoborohydride in a solvent such as methanol, ethanol or the like, or by treatment of tetracyclic amines (I, $R^1=H$) with an alkylating agent, for example, allyl or benzyl bromide. Alternatively, alkylation of tetracyclic amides (31) followed by reduction of the N-alkylated tetracyclic amides (32) using lithium aluminum hydride or diborane, in a solvent such as ether or tetrahydrofuran may provide N-alkylated tetracyclic amines (I, $R^1 \neq H$).

The present invention encompass also novel intermediates useful in the preparation of compounds of the formula I which are those of formulae below:

$(+)$, $(-)$, or $(+/-)$-$(4a\alpha,10\alpha,10a\alpha)$-1,3,4,9,10,10a-hexahydro-2H-4a,10-(iminomethano)phenanthrene-9,11-dione, $(+)$, $(-)$, or $(+/-)$-$(4a\alpha,10\alpha,10a\alpha)$-1,2,3,4,10,10a-hexahydro-6-methoxy-9H-4a,10-(iminomethano)-phenanthrene-9,11-dione, (+), (−), or (+/−)-(4aα,10α,10aα)-1,3,4,9,10,10a-hexahydro-2H-4a,10-(iminomethano)phenanthrene-11-one, (+), (−), or (+/−)-(4aα,10α,10aα)-1,3,4,9,10,10a-hexahydro-6-methoxy-2H-4a,10-(iminomethano)-phenanthrene-11-one, (+), (−), or (+/−)-(4aα,9α,10aα)-1,3,4,9,10,10a-hexahydro-4a,9(4H)-phenanthrenedicarboxylic, (+), (−), or (+/−)-(4aα,9α,10aα)-1,3,4,9,10,10a-hexahydro-6-methoxy-4a,9(4H)-phenanthrenedicarboxylic, (+/−)-(4aα,9β,10aα)-1,9,10,10a-Tetrahydro-4a-9(4H)-phenanthrenedicarboxylic acid, (+/−)-(4aα,9β,10aα)-1,9,10,10a-Tetrahydro-6-methoxy-4a,9(4H)-phenanthrenedicarboxylic acid, (+/−)-(4aα,9α,10aα)-1,3,4,9,10,10a-hexahydro-2H-4a 9-(methoxymethano)phenanthrene-11,13-dione, (+), (−), or (+/−)-(4aα,9α,10aα)-1,3,4,9,10,10a-hexahydro-6-methoxy-2H-4a,9-(methoxymethano)-phenanthrene-11,13-dione, 9-methyl (+), (−), or (+/−)-(4aα,9α,10aα)-1,3,4,9,10,10a-hexahydro-4a,9(2H)-phenanthrenedicarboxylate, 9-methyl (+), (−), or (+/−)-(4aα,9α,10aα)-1,3,4,9,10,10a-hexahydro-6-methoxy-4a,9(2H)-phenanthrenedicarboxylate, (+/−)-(4aα,9β,10aα) 1,3,4,9,10,10a-Hexahydro-4a,9(4H)-phenanthrenedicarboxylic acid, (+/−)-(4aα,9β,10aα)-1,3,4,9,10,10a-Hexahydro-4a,9(4H)-phenanthrenedicarboxylic acid, methyl (+), (−), or (+/−)-(4aα,9α,10aα)-1,2,3,4,4a,9,10,10a-octahydro-4a-[(methoxycarbonyl)-amino]-9-phenanthrenecarboxylate, methyl (+), (−), or (+/−)-(4aα,9α,10aα)-1,2,3,4,4a,9,10,10a-octahydro-6-methoxy-4a-[(methoxycarbonyl)amino]-9-phenanthrene-carboxylate, (+), (−), or (+/−) (4aα,9α,10aα)-4a-amino-1,2,3,4,4a,9,10,10a-octahydro-9-phenanthrenecarboxylic acid, (+), (−), or (+/−) (4aα,9α,10aα)-4a-amino-1,2,3,4,4a,9,10,10a-octahydro-6-methoxy-9-phenanthrenecarboxylic acid, (+), (−), or (+/−)-(4aα,9α,10aα)-1,3,4,9,10,10a-hexahydro-2H-4a,9-(iminomethano)phenanthren-11-one, and (+), (−), or (+/−) (4aα,9α,10aα)-1,3,4,9,10,10a-hexahydro-6-methoxy 2H-4a,9-(iminomethano)phenanthren-11-one.

The compounds of the present invention can be administered in a wide variety of oral and parenteral dosage forms. It will be obvious to those skilled in the art that the following dosage forms may comprise as the active component, either a compound of formula I or a corresponding pharmaceutically acceptable salt of a compound of formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For example, parenteral injection liquid preparations can be formulated in solution in aqueous polyethylene glycol solution.

Aqueous solutions suitable for oral use can be prepared by dissolving the active component in water and adding suitable colorants, flavors, stabilizing and thickenings agents, as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg preferably 10 mg to 100 mg according to the particular application and the potency of the active component. The composition can, if desired, also contain other compatible therapeutic agents.

In therapeutic use as antiischemic agents, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the present invention.

EXAMPLE 1

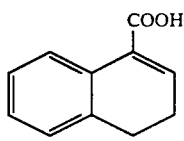

3,4 Dihydro-1-napthlenecarboxylic acid

A solution of 1 napthoic acid (600 g, 3.48 mol) in 1.5 L of ether was added dropwise to 5 L of liquid ammonia at −78° C. The resulting suspension was treated with 200 g of sodium metal over a 30 minute period. Additional sodium metal (40 g) was added during the next 30 minutes. The reaction mixture was warmed to room temperature over an 18-hour period under a stream of nitrogen to remove ammonia. An additional 5 L of ether and 400 g of solid NH$_4$Cl were added cautiously followed by 400 Ml of ethanol. Water was added followed by saturated aqueous NH$_4$Cl solution. The resulting solution was made acidic Ph=1.5 using concentrated Hcl. The organic layer was separated and the aqueous layer was extracted with ether. The combined organic extracts were concentrated and the residue (660 g) was dissolved in 6 L of 10% KOH solution and heated at 105° C. The resulting solution was cooled to room temperature and made acidic Ph=1.5 with concentrated Hcl solution. The aqueous phase was extracted with ether (5×1000 Ml). The combined organic extracts were concentrated to give the title compound as a white solid (470 g, 77%).

EXAMPLE 2

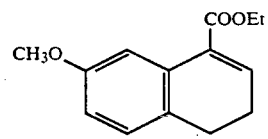

Ethyl 3,4-Dihydro-7-methoxy-1-napthlene carboxylate

A solution of 7-methoxy-1-tetralone (80.7 g, 0.458 mol) was dissolved in 200 mL of CH$_2$Cl$_2$. The resulting solution was cooled to 0° C. and a catalytic amount of ZnI$_2$ was added followed by the slow addition of trimethylsilyl cyanide (50 g, 0.50 mol). The reaction mixture was warmed to room temperature and stirred for 24 hours. The resulting solution was added slowly to a saturated solution of HCl in ethanol at 0° C. The resulting solution was stirred for 24 hours at 0° C. and concentrated. The solid that was obtained was treated with 800 mL of 1N sulfuric acid and 200 mL of ether and stirred at room temperature for 24 hours. The organic phase was collected and the aqueous phase was extracted with additional ether. The combined organic phases were dried and concentrated to give ethyl 1,2,3,4-tetrahydro-1-hydroxy-7-methoxy-1-napthlene carboxylate (60.0 g, 56%). This material was added to a refluxing solution of toluenesulfonic acid (64 g) in 750 mL of toluene The resulting solution was heated to reflux for 15 minutes, cooled to room temperature and washed with saturated aqueous sodium bicarbonate (100 mL), dried and concentrated to give the title compound as an oil (45 g, 86%).

EXAMPLE 3

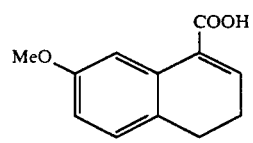

3,4-Dihydro-7-methoxy-1 napthlene carboxylic acid 2

A solution of the product from Example 2 (45 g, 0.194 mol) in 500 mL of aqueous 1N NaOH solution was heated at reflux for 18 hours. The reaction mixture was cooled to room temperature and diluted with water (500 mL). The aqueous phase was extracted with CH$_2$Cl$_2$(5×25 mL) and acidified with aqueous HCl solution. The solution was cooled in an ice bath and the solid which precipitated was collected and dried in vacuo at 60° C. to give the title compound as a solid (39.5 g, 99%) mp 115° C.

EXAMPLE 4

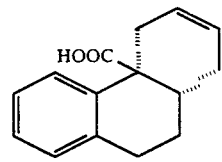

Cis-1,9,10,10a-tetrahydro-4a(4H) phenanthrene carboxylic acid

To a solution of 3,4-dihydronapthlene-1-carboxylic acid (29.7 g, 0.170 mol) in toluene (75 mL) was added butadiene (16 g) and a trace of butyrated hydroxy toluene (BHT). The solution was heated to 180° C. for 18 hours in a sealed reactor, then chromatographed twice over silica gel. Recrystallization from ethyl acetate/heptane affords the title compound as a colorless crystalline solid (10.5 g, 27%). The recovered starting material was reacted with butadiene to afford, after workup, additional title product (8.0 g, 21%).

EXAMPLE 5

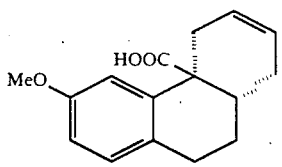

Cis-1,9,10,10a-tetrahydro-6-methoxy-4a(4H)-phenanthrene carboxylic acid

In a manner similar to that described in Example 4, the product of Example 3 (35.9 g, 0.146 mol) was converted to the title compound (22 g, 44%) as a white solid mp 125° C.

EXAMPLE 6

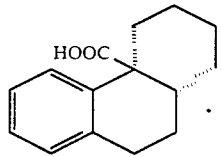

Cis-1,3,4,9,10,10a-Hexahydro-4a(2H)phenanthrene-carboxylic acid

A solution of the product from Example 4 (27.4 g, 0.120 mol) in methanol was hydrogenated over 5% palladium on carbon (2.5 g). The reaction mixture was concentrated to give the title compound (24.3 g, 88%) as a white solid mp 142°-144° C.

EXAMPLE 7

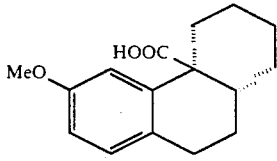

Cis-1,3,4,9,10,10a-Hexahydro-6-methoxy-4a(2H)-phenanthrene carboxylic acid

In a manner similar to that described in Example 6, the product from Example 5 (3.03 g, 11.7 mmol) was converted to the title compound (2.5 g, 83%) as a white solid mp 171°-173° C.

EXAMPLE 8

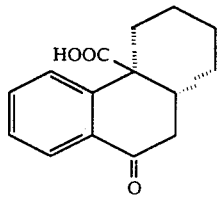

Cis-1,3,4,9,10,10a-Hexahydro-9-oxo-4a(2H)phenanthrene carboxylic acid

A solution of the compound from Example 6 (42 g, 0.182 mol) in 900 mL glacial acetic acid was treated dropwise with a solution of chromium trioxide (91 g, 0.912 mol) in 850 mL of glacial acetic acid and 50 mL of water. The reaction was stirred at room temperature for 5 hours and concentrated. The residue was partitioned between benzene and water. The aqueous layer was saturated with NaCl and extracted with additional benzene. The combined organic layers were dried (MgSO$_4$), filtered and concentrated to give a brown solid (37 g). The solid was suspended in 150 mL ethyl acetate and collected by suction filtration, and washed with additional ethyl acetate. The resulting material was dried under vacuum to give the title compound (21.0 g, 47%) as a white solid.

EXAMPLE 9

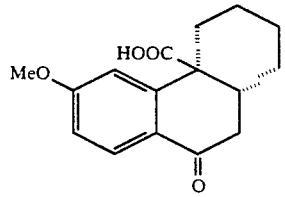

(+/−)-Cis-1,3,4,9,10,10ahexahydro-6 methoxy-9-oxo-4a (2H)phenanthrenecarboxylic acid In a manner similar to that described in Example 8 the product from Example 7 is converted to the title compound.

EXAMPLE 10

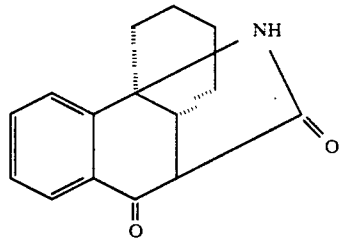

(+/−)-(4aα,10α,10aα)-1,3,4,9,10,10a Hexahydro-2H-4a,10-(iminomethano)phenanthrene-9,11-dione A solution of the compound from Example 8 (3.09 g, 12.6 mmol), triethylamine (1.45 g, 14.3 mmol), and diphenylphosphorylazide (3.58 g, 13.9 mmol) in 150 mL of toluene was heated at 100° C. for 48 hours. The reaction mixture was cooled to room temperature and washed with saturated aqueous NaHCO$_3$ (50 mL). The organic phase was dried (MgSO$_4$), filtered, and concentrated. The residue was purified by chromatography (silica gel, 3:1 CHCl$_3$EtOAc). The product was recrystallized from hot 2-pentanone to give the title compound (1.93 g, 63%) mp 228°-230° C.

Anal. (C$_{15}$H$_{15}$NO$_2$).
Calc'd: 74.67; H, 6.27; N, 5.81.
Found: C, 74.46; H, 6.29; N, 5.75.

EXAMPLE 11

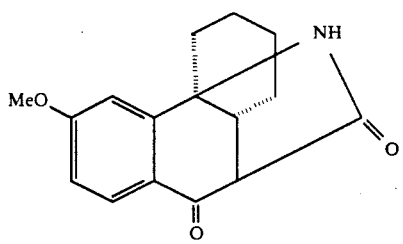

(+/−)-(4aα,10α,10aα)-1,2,3,4,10,10a-Hexahydro-methoxy-9H-4a,10-(iminomethano)phenanthrene-9,11-dione In a manner similar to that described in Example 10 the product from Example 9 is converted to the title compound.

EXAMPLE 12

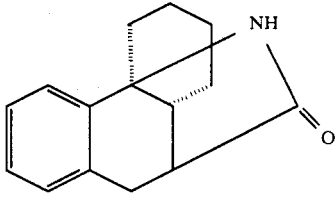

(+/−)-(4aα,10α,10aα)-1,3,4,9,10,10a-Hexahydro-2H-4a,10-(iminomethano)phenanthrene-11-one A solution of the compound from Example 10 (2.30 g, 9.53 mmol) in acetic acid (100 mL) and concentrated sulfuric acid (1 drop) was hydrogenated at 50 psi over 20% palladium on carbon (0.5 g) for 4 hours. The reaction mixture was concentrated and the residue was dissolved in $CH_2Cl_2$ (300 mL) and washed with saturated aqueous $NaHCO_3$ solution (20 mL). The organic phase was dried ($MgSO_4$), filtered and concentrated. The residue was suspended in a solution of heptane/toluene (5:1) and the solid was collected by suction filtration and dried under vacuum. The title compound was isolated as a white solid (1.92 g, 90%) mp 184°–186° C.

Anal. ($C_{15}H_{17}NO$).
Calc'd: C, 79.26; H, 7.54; N, 6.16.
Found: C, 79.14; H, 7.45; N, 5.80.

EXAMPLE 13

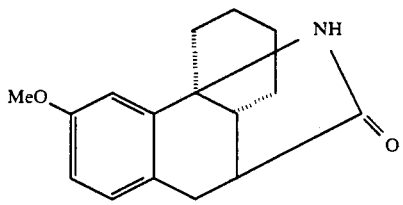

(+/−)-(4aα,10α,10aα)-1,3,4,9,10,10a-Hexahydro-6-methoxy-2H 4a,10-(iminomethano)phenanthrene-11-one In a manner similar to that described in Example 12 the product from Example 11 is converted to the title compound.

EXAMPLE 14

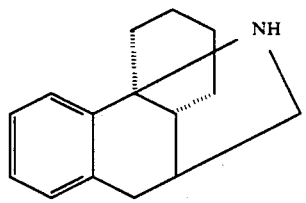

(+/−)-(4aα,10α,10aα) 1,3,4,9,10,10a Hexahydro-2H-4a,10-(iminomethano)phenanthrene A solution of the compound from Example 12 (0.96 g, 4.22 mmol) in 10 mL of THF was added dropwise to a suspension of lithium aluminum hydride (0.80 g, 21.1 mmol) in 10 mL of THF. The resulting suspension was heated to reflux for 1 hour, and stirred at room temperature for 24 hours. The reaction mixture was quenched with small portions of $Na_2SO_4$-$10H_2$) until no further gas evolution was observed. The resulting suspension was filtered and the filtrate was concentrated to give the title compound (0.73 g, 82%) as a white solid. An analytical sample was prepared by crystallization of the fumarate salt from acetone mp 213° C.

Anal. ($C_{15}H_{19}N.C_4H_4O_4$).
Calc'd: C, 69.28; H, 7.04; N, 4.25.
Found: C, 68.96; H, 6.81; N, 4.20.

EXAMPLE 15

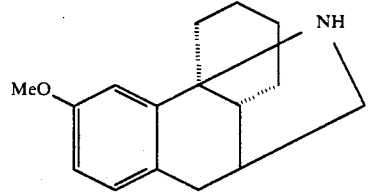

(+/−)-(4aα,10α,10aα) 1,3,4,9,10,10a-Hexahydro-6-methoxy-2H-4a,10-(iminomethano)phenanthrene In a manner similar to that described in Example 14 the product from Example 13 is converted to the title compound.

EXAMPLE 16

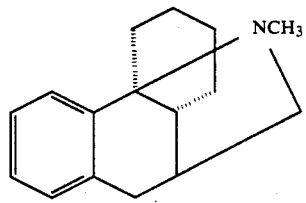

(+/−)-(4aα,10α,10aα)
1,3,4,9,10,10a-Hexahydro-12-methyl-2H
4a,10-(iminomethano)phenanthrene A solution of the compound from Example 14 (0.41 g, 1.92 mmol) in 10 mL of methanol and 2 mL of 37% aqueous formaldehyde was treated with NaBH₃CN (0.4 g) and stirred at room temperature for several hours. Workup followed by chromatography (silica gel, 15:1:0.1 CHCl₃/MeOH/NH₄OH) provided the title compound (0.27 g, 62%) as an oil. An analytical sample was prepared by crystallization of the fumarate salt from acetone, mp 195°–197° C.

Anal. (C₁₆H₂₁N.C₄H₄O₄).
Calc'd: C, 69.95; H, 7.34; N, 4.08.
Found: C, 70.09; H, 7.39; N, 4.29.

EXAMPLE 17

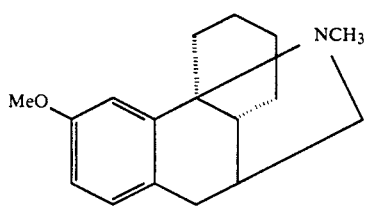

(+/−)-(4aα,10α,10aα)-1,3,4,9,10,10a
Hexahydro-6-methoxy-12-methyl-2H-4a,10-(iminomethano)phenanthrene In a manner similar to that described in Example 16 the product from Example 15 is converted to the title compound.

EXAMPLE 18

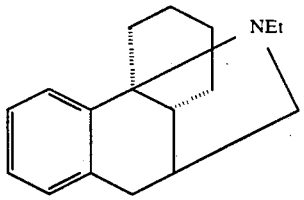

(+/−)-(4aα,10α,10aα)-12-Ethyl-1,3,4,9,10,10a-hexahydro-2H-4a,10-(iminomethano)phenanthrene In a manner similar to that described in Example 16, the product from Example 14 (0.46 g, 2.16 mmol) and acetaldehyde (0.47 g, 10.8 mmol) was converted to the title compound (0.38 g, 73%) as an oil. An analytical sample was prepared by crystallization of the fumarate salt from acetone, mp 185°–186° C.

Anal. (C₁₇H₂₃N.C₄H₄O₄).
Calc'd: C, 70.56; H, 7.61; N, 3.92.
Found: C, 70.47; H, 7.59; N, 4.10.

EXAMPLE 19

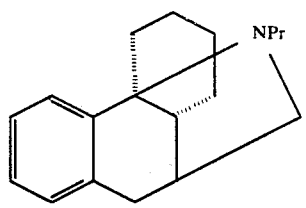

(+/−)-(4aα,10α,10aα)-1,3,4,9,10,10a-Hexahydro-12-propyl-2H-4a,10-(iminomethano)phenanthrene In a manner similar to that described in Example 16, the product from Example 14 (0.42 g, 1.95 mmol) and propionaldehyde (0.17 g, 9.75 mmol) was converted to the title compound (0.36 g, 72%) as an oil. Treatment of the title compound in ether with a solution of HBr in ether provided the HBr salt as a white solid, mp 229°–231° C.

Anal. (C₁₈H₂₅N.HBr).
Calc'd: C, 64.28; H, 7.79; N, 4.16; Br, 23.76.
Found: C, 63.87; H, 7.73; N, 4.28; Br, 23.56.

EXAMPLE 20

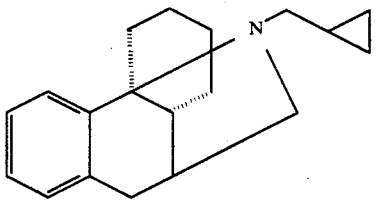

(+/−)-(4aα,10α,10aα)-12-(Cyclopropylmethyl)-1,3,4,9,10,10a-hexahydro-2H-4a,10-(iminomethano)-phenanthrene In a manner similar to that described in Example 16, the product from Example 14 (0.32 g, 1.50 mmol) and cyclopropylcarboxaldehyde (0.52 g, 7.5 mmol) were reacted to give the title compound (0.26 g, 65%) as an oil. A sample of the fumarate salt was prepared by crystallization from acetone, mp 189°–191° C.

Anal. (C₁₉H₂₅N.C₄H₄O₄).
Calc'd: C, 72.04; H, 7.62; N, 3.65.
Found: C, 71.82; H, 7.64; N, 3.15.

EXAMPLE 21

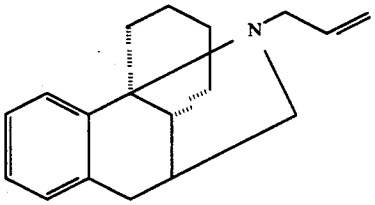

(+/−)-(4aα,10α,10aα)-1,3,4,9,10,10a-Hexahydro-12-(2-propenyl)-2H-4a,10-(iminomethano)phenanthrene A solution of the product from Example 14 (0.40 g, 1.88 mmol) in CH₂Cl₂ was treated with allyl bromide (0.22 g, 1.85 mmol). Workup as described in Example 15 gave the title compound (0.26 g, 54%) as an oil. A sample of the fumarate salt was prepared by crystallization from acetone, mp 183° C.

Anal. (C$_{18}$H$_{23}$N.C$_4$H$_4$O$_4$).
Calc'd: C 71.52; H 7 37; N, 3.79.
Found: C, 71.72; H, 7.45; N, 3.96.

EXAMPLE 22

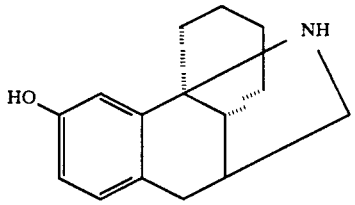

(+/−)-(4aα,10α,10aα)-1,3,4,9,10,10a Hexahydro-2H-4a,10-(iminomethano)phenanthren-6-ol A solution of the product from Example 15 is heated to reflux in 48% aqueous HBr until the starting material is consumed. The reaction mixture is poured into cold NH$_4$OH solution. The resulting solution is extracted with ethyl acetate, dried, and concentrated to give the title compound.

EXAMPLE 23

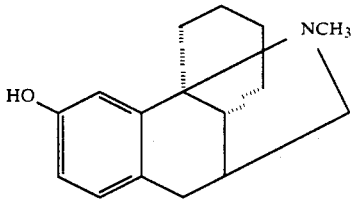

(+/−)-(4aα,10α,10aα)-1,3,4,9,10,10a-Hexahydro-12-methyl-2H-4a,10-(iminomethano)phenanthren-6-ol In a manner similar to that described in Example 22, the product of Example 17 is converted to the title compound.

EXAMPLE 24

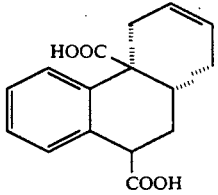

(+/−)-(4aα,9α,10aα)-1,9,10,10a-Tetrahydro-4a,9(4H)-phenanthrenedicarboxylic acid and
(+/−)-(4aα,9β,10aα)-1,9,10,10a-Tetrahydro-4a-9(4H)-phenanthrene-dicarboxylic acid A solution of 1,2-dihydro-1,4-napthlene-dicarboxylic acid (prepared by the method of Lyssy in *J. Org. Chem.* 5, (1962); 1.0 eq), butyrated hydroxytoluene (0.05 eq), and butadiene (20 eq) in toluene is pressurized with nitrogen (1900 psi) in a reaction vessel and heated to 150° C. until the starting material is consumed. Workup, followed by purification affords the title compounds.

EXAMPLE 25

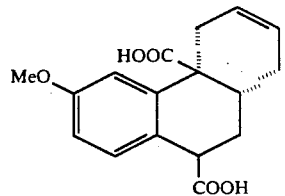

(+/−)-(4aα,9α,10aα)-1,9,10,10a-Tetrahydro-6-methoxy-4a,9(4H)-phenanthrenedicarboxylic acid and
(+/−)-(4aα,9β,10aα)-1,9,10,10a-Tetrahydro-6-methoxy-4a,9(4H)-phenanthrenedicarboxylic acid In a manner similar to that described in Example 24, the 1,2-dihydro-6-methoxy-1,4-napthlene-dicarboxylic acid is converted to the title compounds.

EXAMPLE 26

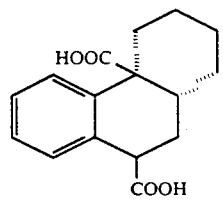

(+/−)-(4aα,9α,10aα) 1,3,4,9,10,10a-Hexahydro-4a,9(4H)-phenanthrenedicarboxylic acid and
(+/−)-(4aα,9β,10aα)-1,3,4,9,10,10a-Hexahydro-4a,9(4H)-phenanthrene-dicarboxylic acid A solution of the product from Example 24 in methanol is hydrogenated using 10% palladium on carbon. The reaction mixture is concentrated to give the title compound.

EXAMPLE 27

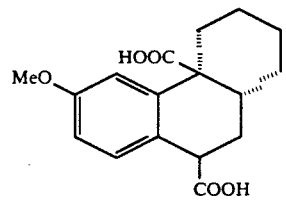

(+/−)-(4aα,9α,10aα)-1,3,4,9,10,10a-Hexahydro-6-methoxy-4a,9(4H)-phenanthrenedicarboxylic acid and
(+/−)-(4aα,9β,10aα)-1,3,4,9,10,10a-Hexahydro-4a,9(4H)-phenanthrenedicarboxylic acid In a manner similar to that described in Example 26, the product from Example 25 is converted to the title compounds.

EXAMPLE 28

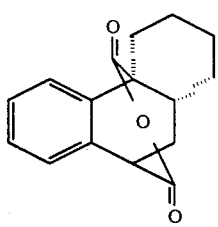

(+/−)-(4aα,9α,10aα)-1,3,4,9,10,10a-Hexahydro-2H-4a,9-(methoxymethano)phenanthrene-11,13-dione A solution of the product from Example 26 and toluene sulphonic acid are dissolved in toluene and the resulting solution is heated at reflux with removal of water (Dean-Stark trap). The resulting solution is cooled to room temperature and washed with bicarbonate solution. The organic phase is dried and concentrated. Purification of the residue affords the title compound.

EXAMPLE 29

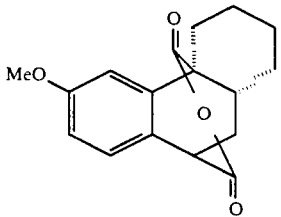

(+/−)-(4aα,9α,10aα)-1,3,4,9,10,10a-Hexahydro-6-methoxy-2H-4a,9-(methoxymethano)phenanthrene 11,13-dione In a manner similar to that described in Example 28, the product from Example 27 is converted to the title compound.

EXAMPLE 30

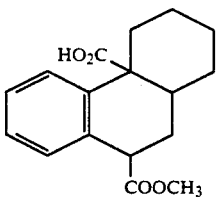

9-Methyl (+/−)-(4aα,9α,10aα)-1,3,4,9,10,10a-hexahydro-4a,9(2H)-phenanthrenedicarboxylate A solution of product from Example 28 in methanol is added to a solution of sodium methoxide (1 eq) in methanol. The resulting solution is heated at reflux until the starting material is consumed. The reaction mixture is concentrated and the residue is treated with water. The aqueous phase is acidified (pH=2) using 1N HCl solution and extracted with ether. The organic extracts are dried and concentrated. The residue is purified to give the title compound.

EXAMPLE 31

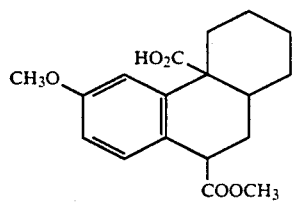

9-Methyl (+/−)-(4aα,9α,10aα)-1,3,4,9,10,10a-hexahydro-6-methoxy-4a,9(2H)-phenanthrenedicarboxylate In a manner similar to that described in Example 30, the product from Example 29 is converted to the title compound.

EXAMPLE 32

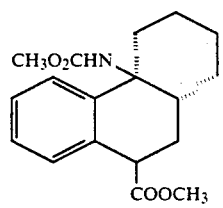

Methyl (+/−)-(4aα,9α,10aα)-1,2,3,4,4a,9,10,10a-octahydro-4a-[(methoxycarbonyl)amino]-9-phenanthrenecarboxylate A solution of the product from Example 30 (1.0 eq) and triethylamine (1.1 eq) in toluene is treated with diphenylphosphoryl azide (1.0 eq). The resulting solution is heated to 100° C. for 30 minutes and then cooled to room temperature. Methanol is added the resulting solution is heated to reflux for hours. Workup followed by chromatography give the title compound.

EXAMPLE 33

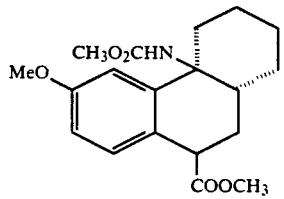

Methyl (+/−)-(4aα,9α,10aα)-1,2,3,4,4a,9,10,10a-octahydro-6-methoxy-4a-[(methoxycarbonyl)amino]-9-phenanthrenecarboxylate In a manner similar to that described in Example 32, the product from Example 31 is converted to the title compound.

EXAMPLE 34

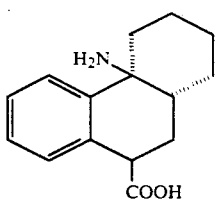

(+/−)-(4aα,9α,10aα)-4a-Amino-1,2,3,4,4a,9,10,10a-octahydro-9-phenanthrenecarboxylic acid A solution of the product from Example 32 (1.0 eq) and potassium trimethylsilanoate (5.0 eq) in THF is heated to reflux for 24 hours. The reaction mixture is concentrated and the residue is treated with water. The aqueous phase is acidified (pH=7-8) using 1 N HCl solution and is then extracted with $CH_2Cl_2$. The organic extracts are dried and concentrated to give the title compound.

EXAMPLE 35

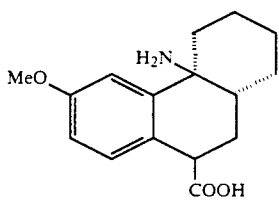

(+/−) (4aα,9α,10aα) 4a-Amino-1,2,3,4,4a,9,10,10a-octahydro-6-methoxy-9-phenanthrenecarboxylic acid In a manner similar to that described in Example 34, the product from Example 33 is converted to the title compound.

EXAMPLE 36

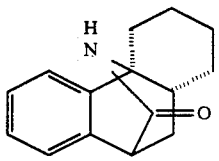

(+/−) (4aα,9α,10aα)-1,3,4,9,10,10a-Hexahydro-2H-4a,9-(iminomethano)phenanthren-11-one The product from Example 34 in toluene is heated at reflux with removal of water until the starting material is consumed. The reaction mixture is concentrated. Purification of the residue provides the title compound.

EXAMPLE 37

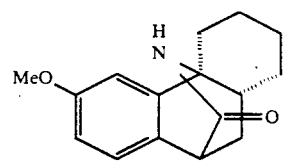

(+/−)-(4aα,9α,10aα)-1,3,4,9,10,10a-6-methoxy-2H-4a,9-(iminomethano)phenanthren-11-one In a manner similar to that described in Example 36, the product from Example 35 is converted to the title compound.

EXAMPLE 38

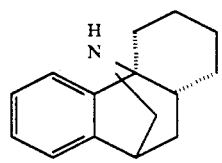

(+/−)-(4aα,9α,10aα)-1,3,4,9,10,10a-Hexahydro-2H-4a,9-(iminomethano)phenanthrene

In a manner similar to that described in Example 14, the product from Example 36 is converted to the title compound.

EXAMPLE 39

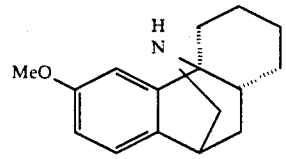

(+/−)-(4aα,9α,10aα)-1,3,4,9,10,10a-Hexahydro-6-methoxy-2H-4a,9-(iminomethano)phenanthrene In a manner similar to that described in Example 14, the product from Example 37 is converted to the title compound.

EXAMPLE 40

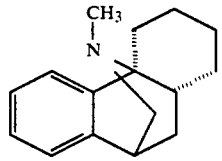

(+/−)-(4aα,9α,10aα)-1,3,4,9,10,10a-Hexahydro-12-methyl-2H-4a,9-(iminomethano)phenanthrene In a manner similar to that described in Example 16, the product from Example 38 is converted to the title compound.

EXAMPLE 41

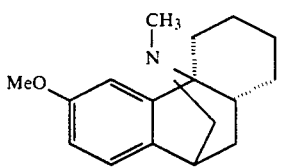

(+/−)-(4aα,9α,10aα,1,3,4,9,10,10a-Hexahydro-12-methyl-6-methoxy-2H 4a,9-(iminomethano)phenanthrene In a manner similar to that described in Example 16, the product from Example 39 is converted to the title compound.

EXAMPLE 42

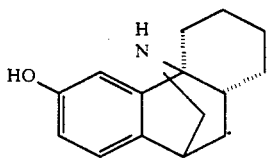

(+/−)-(4aα,9α,10aα)-1,3,4,9,10,10a-Hexahydro-2H-4a,9-(iminomethano)phenanthren-6-ol In a manner similar to that described in Example 22, the product from Example 39 is converted to the title compound.

EXAMPLE 43

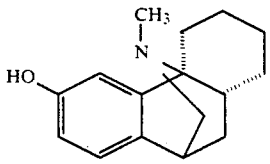

(+/−)-(4aα,9α,10aα)-1,3,4,9,10,10a-Hexahydro-12-methyl-2H-4a,9-(iminomethano)phenanthren-6-ol)

In a manner similar to that described in Example 22, the product from Example 41 is converted to the title compound.

We claim:

1. A compound of the formula

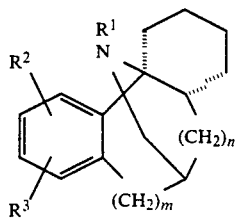

or a pharmaceutically acceptable acid addition salt thereof wherein:

$R^1$ is hydrogen, loweralkyl, loweralkenyl, loweralkynyl, phenyl- or thienyl- loweralkyl, cycloalkylloweralkyl, or a pharmaceutically acceptable labile group;

$R^2$ and $R^3$ are each independently hydrogen, loweralkyl, hydroxy, loweralkoxy, trifluoromethyl, halogen, amino, monoloweralkyl, or diloweralkylamino, and when m is 1, n is 0.

2. A compound according to claim 1, wherein
$R^1$ is hydrogen, loweralkyl, loweralkenyl, or cyclopropylmethyl;
$R^2$ and $R^3$ are each independently hydrogen, loweralkyl, hydroxy, or loweralkoxy;
m is 1 and n is 0.

3. A compound selected from the group consisting of:
(+), (−), or (+/−) (4aα,10α,10aα)-1,3,4,9,10,10a-hexahydro-2H-4a,10-iminomethano)phenanthrene,
(+/−)-(4aα,10α,10aα)-1,3,4,9,10,10a-hexahydro-6-methoxy-2H-4a,10-(iminomethano)phenanthrene,
(+), (−), or (+/−)-(4aα,10α,10aα)-1,3,4,9,10,10a hexahydro 12 methyl-2H-4a,10-(iminomethano)phenanthrene hydrochloride,
(+), (−), or (+/−)-(4aα,10α,10aα)-1,3,4,9,10,10a-hexahydro-6-methoxy-12-methyl-2H-4a,10-(iminomethano)phenanthrene,
(+), (−), or (+/−)-(4aα,10α,10aα)-12-ethyl-1,3,4,9,10,10a-hexahydro-2H 4a,10-(iminomethano)phenanthrene,
(+), (−), or (+/−)-(4aα,10α,10aα)-1,3,4,9,10,10a-hexahydro 12-propyl-2H-4a,10-(iminomethano)phenanthrene hydrochloride,
(+), (−), or (+/−)-(4aα,10α,10aα)-12-(cyclopropylmethyl)-1,3,4,9,10,10a-hexahydro-2H-4a,10-(iminomethano)phenanthrene,
(+), (−), or (+/−)-(4aα,10α,10aα)-1,3,4,9,10,10a-hexahydro-12-(2-propenyl)-2H-4a,10-(iminomethano)phenanthrene,
(+), (−), or (+/−)-(4aα,10α,10aα)-1,3,4,9,10,10a-hexahydro-12-methyl-2H-4a,10-(iminomethano)phenanthren-6-ol.
(+), (−), or (+/−)-(4aα,10α,10aα)-1,3,4,9,10,10a-hexahydro-12-methyl-2H-4a,10-(iminomethano)phenanthren-6-ol.

4. A compound selected from the group consisting of:
(+), (−), or (+/−)-(4aα,10α,10aα)-1,3,4,9,10,10a-hexahydro-2H-4a,10-(iminomethano)phenanthrene-9,11-dione,
(+), (−), or (+/−)-(4aα,10α,10aα)-1,3,4,9,10,10a-hexahydro-6-methoxy-2H-4a,10-(iminomethano)-phenanthrene-9,11-dione,
(+), (−), or (+/−)-(4aα,10α,10aα)-1,3,4,9,10,10a-hexahydro-2H-4a,10-(iminomethano)phenanthrene-11-one,
(+), (−), or (+/−)-(4aα,10α,10aα)-1,3,4,9,10,10a-hexahydro-6-methoxy-2H-4a,10-(iminomethano)-phenanthrene-11-one, 5. A pharmaceutical composition comprising a therapeutically effective amount of a compound of claim 1 together with a pharmaceutically acceptable carrier.

6. A method for treating cerebrovascular disorders which comprises administering to a patient in need thereof the pharmaceutical composition in claim 5 in unit dosage form.

7. A method for treating disorders responsive to the blockade of glutamic and aspartic acid receptors which comprises administering to a patient in need thereof the pharmaceutical composition of claim 5 in unit dosage form.

8. A method for treating stroke which comprises administering to a patient in need thereof the pharmaceutical composition of claim 5 in unit dosage form.

* * * * *

UNITED STATES PATENT AND TRADEMARK OFFICE
CERTIFICATE OF CORRECTION

PATENT NO. : 5,141,934

DATED : August 25, 1992

INVENTOR(S) : Graham Johnson et al

It is certified that error appears in the above-indentified patent and that said Letters Patent is hereby corrected as shown below:

Column 32, line 36, delete "12-methyl".

Column 32, line 37, after "nanthren-6-ol" add ", and".

Signed and Sealed this

Twenty-fourth Day of August, 1993

*Attest:*

BRUCE LEHMAN

*Attesting Officer*     *Commissioner of Patents and Trademarks*